US006294495B1

(12) United States Patent
Matsunaga

(10) Patent No.: US 6,294,495 B1
(45) Date of Patent: Sep. 25, 2001

(54) TRIDENTATE LIGAND-CONTAINING METAL CATALYST COMPLEXES FOR OLEFIN POLYMERIZATION

(75) Inventor: Phillip T. Matsunaga, Houston, TX (US)

(73) Assignee: ExxonMobil Chemicals Patent Inc., Houston, TX (US)

( * ) Notice: Subject to any disclaimer, the term of this patent is extended or adjusted under 35 U.S.C. 154(b) by 0 days.

(21) Appl. No.: 09/302,243

(22) Filed: Apr. 29, 1999

Related U.S. Application Data

(60) Provisional application No. 60/083,966, filed on May 1, 1998.

(51) Int. Cl.$^7$ .............................. B01J 31/00; B01J 37/00; C08F 4/02; C08F 4/60; C08F 4/44

(52) U.S. Cl. ..................... 502/103; 502/117; 502/153; 502/154; 502/155; 502/162; 502/165; 502/166; 502/167; 526/134; 526/160; 526/161; 526/172

(58) Field of Search ................................ 502/103, 117, 502/153, 154, 155, 162, 165, 166, 167; 526/134, 160, 161, 172

(56) References Cited

U.S. PATENT DOCUMENTS

| | | | |
|---|---|---|---|
| 5,318,935 | 6/1994 | Canich et al. | 502/117 |
| 5,374,696 | 12/1994 | Rosen et al. | 526/155 |
| 5,494,874 | 2/1996 | Rosen et al. | 502/155 |
| 5,965,678 | * 10/1999 | Becke et al. | 502/117 |
| 5,969,171 | * 10/1999 | Nestler | 502/155 |
| 5,977,393 | * 11/1999 | Grubbs et al. | 502/162 |

(List continued on next page.)

FOREIGN PATENT DOCUMENTS

| | | |
|---|---|---|
| 0 805 142 A1 | 11/1998 | (EP) . |
| WO 96/13529 | 5/1996 | (WO) . |
| WO 96/23010 | 8/1996 | (WO) . |
| WO 97/17379 | 5/1997 | (WO) . |
| WO 97/42147 | 11/1997 | (WO) . |
| WO 97/42149 | 11/1997 | (WO) . |
| WO 97/42151 | 11/1997 | (WO) . |
| WO 97/42161 | 11/1997 | (WO) . |
| WO 97/42162 | 11/1997 | (WO) . |
| WO 97/42163 | 11/1997 | (WO) . |
| WO 97/42164 | 11/1997 | (WO) . |
| WO 97/42165 | 11/1997 | (WO) . |
| WO 97/42198 | 11/1997 | (WO) . |
| WO 97/42199 | 11/1997 | (WO) . |
| WO 97/42228 | 11/1997 | (WO) . |
| WO 97/42232 | 11/1997 | (WO) . |
| WO 97/42233 | 11/1997 | (WO) . |
| WO 97/42235 | 11/1997 | (WO) . |
| WO 97/42236 | 11/1997 | (WO) . |
| WO 97/42237 | 11/1997 | (WO) . |
| WO 97/42238 | 11/1997 | (WO) . |
| WO 97/42239 | 11/1997 | (WO) . |
| WO 97/42240 | 11/1997 | (WO) . |
| WO 97/45160 | 11/1997 | (WO) . |

OTHER PUBLICATIONS

"Transfer–dehydrogenation Of Alkanes Catalyzed By Rhodium(I) Phosphine Complexes," Wang, K., et al, J. Of Organometallic Chem., vol. 518, No. 1, pp. 55–68, (1996).

Five–and Six–coordinate Ruthenium Complexes With the Tridentate Orthometallated Aryl Bisphosphine Ligand[2,6–($Ph_2PCH_2)_2C_6H_3$], Jia, G., et al, J. Of Organometallic Chem., vol. 534, pp. 173–180, (1997).

New Iron And Cobalt Catalysts For The Polymerization Of Olefins, Small, B., et al, Dept. Of Chemistry–Univ. Of North Carolina at Chapel Hill–Presented at Meeting–America Chemical Society Division Of Polymer Chemistry, vol. 39, No. 1, pp. 213, (1998).

"Intramolecularly Chelated Di– and Tetranuclear Aryllithium Compounds: Crystal Structure of Li2 [C6h4(2–CH2NMe2O]4 Containing Four Center Two Electron–Bonded C(aryl) Atoms and Heptacoordinate Lithium Atoms", van Koten, et al, J. Chem. Soc., vol. 104, pp. 5490–5492 (1982).

"New Dialkylamido Complexes of Transition Metal In Groups 4 and 5 Stabilised by Terdentate Ligands," A. Richard Wills, et al, J. Chem. Soc. Dalton Trans., pp. 1253–1257, (1989).

(List continued on next page.)

Primary Examiner—Mark L. Bell
Assistant Examiner—J. Pasterczyk
(74) Attorney, Agent, or Firm—William G. Muller; Charles E. Runyan

(57) ABSTRACT

An activated tridentate-, monoanionic-ligand-based transition metal catalyst in a reduced oxidation state for olefin polymerization is disclosed. Transition metal catalyst precursors for these catalysts have the formulae:

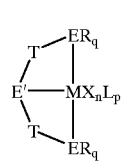

(A)

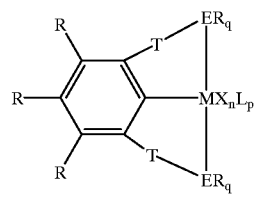

(B)

in which M is a transition metal from Groups 4–9 in a reduced oxidation state, X is a mono anionic ligand, L is a neutral donor group, E is a neutral donor group from Groups 15 and 16, E' is a monoanionic donor group from Group 15, T is a bridging group, n is 1–3 as needed to balance the charge on M, p is 0–3 and q is 1–2. Olefin polymerization is exemplified.

14 Claims, No Drawings

U.S. PATENT DOCUMENTS

| | | | |
|---|---|---|---|
| 5,981,783 | * 11/1999 | Polt | 502/165 |
| 5,998,645 | * 12/1999 | Nestler | 502/155 |
| 6,034,259 | * 3/2000 | Brookhart et al. | 502/155 |
| 6,060,568 | * 5/2000 | Cavell et al. | 502/117 |
| 6,060,569 | * 5/2000 | Bennett et al. | 502/155 |
| 6,069,110 | * 5/2000 | Klaui et al. | 526/134 |
| 6,096,676 | * 8/2000 | Murray | 502/155 |
| 6,103,658 | * 8/2000 | Mackenzie et al. | 502/167 |
| 6,214,761 | * 4/2001 | Bennett | 502/167 |

OTHER PUBLICATIONS

"Organochromium (III) Chemistry: A Neglected Oxidation State," Klaus H. Theopold, Acc. Chem. Res., vol. 23, pp. 263–270, (1990).

"The 1992 Alcan Award Lecture Excursions Around The Periodic Table: Ligand Design In Inorganic Chemistry," Michael O. Fryzuk, Can. J. Chem., vol. 70, pp. 2839–2845, (1992).

"Polymerization Of α–Olefins By Chelating Diamide Complexes Of Titanium," John D. Scollard, et al, Macromolecules, vol. 29, pp. 5241–5243, (1996).

"Novel Olefin Polymerization Catalysts Based On Iron And Cobalt," George J. Britovsek, et al, Chem. Commun., pp. 849–851, (1998).

* cited by examiner

TRIDENTATE LIGAND-CONTAINING METAL CATALYST COMPLEXES FOR OLEFIN POLYMERIZATION

This application claims benefit of provisional application No. 60/083,966, filed May 1, 1998.

FIELD OF THE INVENTION

The present invention relates to transition metal catalyst systems for olefin polymerization, and more particularly to a reduced oxidation state transition metal catalyst system incorporating a tridentate ligand which is not based on cyclopentadienyl ligands.

BACKGROUND OF THE INVENTION

The use of discrete biscyclopentadienyl-based and monocyclopentadienyl-based metal complexes for the polymerization of olefins is well known in the art. In a few cases, olefin polymerization has been demonstrated starting from discrete catalyst precursor complexes with cyclopentadienyl-based ancillary ligand systems and reduced oxidation state metal centers such as in, for example, U.S. Pat. Nos. 5,374,696 and 5,494,874, both to Rosen, et. al.; WO 96/13529; and Theopold, *Acc. Chem. Res.*, vol. 23, pp.263–270 (1990). However, these catalyst precursor complexes do not exhibit $C_2$ or pseudo-$C_2$ symmetries, useful symmetries with many metallocene catalysts.

Recently, there has been an increased interest in identifying catalytic systems that incorporate non-cyclopentadienyl ancillary ligands. For example, Canich and Turner, U.S. Pat. No. 5,318,935 discloses bisamido Group 4 transition metal compounds and McConville, et. al., *Macromolecules*, vol. 29, p. 5241 (1996), discloses bridged, dianionic, diamide ligands. These catalysts incorporate $d^0$ metals in their highest oxidation states. Both of WO 96/23010 and Gibson, et. al., *Chem. Comm.*, pp. 849–85 (1998), disclose diimine-based ligands for metals in Groups 8–10. These diimine-based ancillary ligands are neutral donor ligands. Other demonstrated examples of catalyst precursor complexes incorporating non-cyclopentadienyl ancillary ligands and reduced oxidation state metals show these compounds to have very low activity, see WO 97/17379.

Organometallic compounds with anionic, non-cyclopentadienyl ligands, including those with reduced oxidation state metal centers and those structurally characterized as having $C_2$ or pseudo-$C_2$ symmetry, are known in the scientific literature. See, for example, Fryzuk, *Can. J. Chem.*, vol. 70, p. 2839 (1992); Edwards, et. al., *J. Chem. Soc., Dalton Trans.*, p. 1253 (1989); and van Koten, et. al., *J. Am. Chem. Soc.*, vol. 104, p. 5490 (1982). However, the teachings of these documents do not suggest potential utility of the compounds as polymerization catalysts or catalyst precursor compounds.

SUMMARY OF THE INVENTION

The present invention is directed to a catalyst complex based on a Group 4–9 first or second row transition metal in a reduced oxidation state and having a tridentate, monoanionic, non-cyclopentadienyl ligand containing Group 15 and/or 16 elements, the complex having been activated for olefin polymerization. The monoanionic tridentate ancillary ligand system consists of two Group 15 or 16 atoms bound to the transition metal through dative bonds and a Group 15 atom or aromatic ring carbon atom covalently bound to the transition metal. The covalently bound atom is linked to the datively bound Group 15 or 16 atoms by bridging groups each containing one or more Group 13–16 elements.

In a preferred embodiment, the present invention is directed to a tridentate catalyst system for the polymerization of α-olefins comprising the reaction product of: (a) an organometallic complex of one of the formulae:

(A)

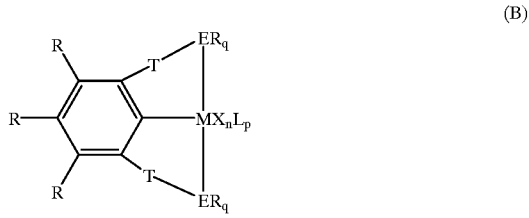

(B)

wherein M is a transition metal from Groups 4–9 in a reduced oxidation state; each X is independently halogen, alkoxide, aryloxide, amide, phosphide, hydride, hydrocarbyl, substituted hydrocarbyl, halocarbyl, substituted halocarbyl, hydrocarbyl- or halocarbyl-substituted organometalloid, or two X groups are joined and bound to the transition metal or an L group to form a ring structure, or one or more of X can contain an L group; L is a neutral donor group which stabilizes the complex; each E is independently a neutral donor group selected from Groups 15 and 16; E' is a monoanionic donor group selected from Group 15; R has the same definition as X but may be the same or different; T is a bridging group containing an element or combination of elements from Groups 13–16; n is a number from 1 to 3 which is determined by counterbalancing the charge on the transition metal such that the transition metal remains in a reduced oxidation state and the overall charge on the complex is neutral; p is a number from 0 to 3 as needed to stabilize the complex; q is 1 or 2 such that E remains a neutral donor group; and (b) a catalyst activator compound. E is preferably selected from N, P, S and O and E' is preferably N or P. M is preferably Ti, V, Cr, Mn, Fe or Co. The catalyst activator compound can be alkylalumoxane, an alkyl aluminum cocatalyst activator, or an ionizing noncoordinating anion precursor compound.

In another aspect, the present invention is directed to a polymerization process characterized by contacting one or more monomers polymerizable by coordination polymerization under suitable coordination polymerization conditions with the catalyst system described above. The monomers can be selected from the group consisting of ethylene, α-olefins, cyclic olefins, non-conjugated diolefins, acetylenically unsaturated monomers, olefinically unsaturated aromatic monomers and $C_{20}$–$C_{200}$ macromonomers. The monomers are preferably at least one member selected from the group consisting of ethylene and $C_3$–$C_{20}$ α-olefins. The catalyst system can also include a solid particulate support.

DETAILED DESCRIPTION OF THE INVENTION

The catalyst precursor transition metal compounds of the present invention can be generically represented by the following chemical formulae:

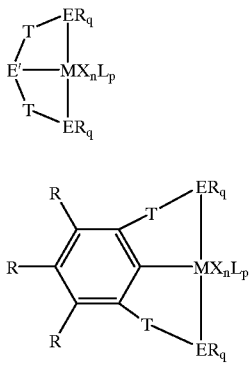

wherein each of the labeled substituents are as defined above.

The transition metal centers can be any metal from Groups 4–9, preferably titanium, vanadium, chromium, manganese, iron or cobalt, in a reduced oxidation state. As used in the specification and the appended claims, "a reduced oxidation state" means an oxidation number which is less than the highest attainable oxidation number of the metal. For example, preferred reduced oxidation state metals include Ti(II), Ti(III), V(II), V(III), V(IV), Cr(II), Cr(III), Cr(IV), Cr(V), Mn(II), Mn(III), Mn(IV), Fe(II), Fe(III), Co(II), Co(III), and the like. More preferred reduced oxidation state metals are those in the +3 oxidation state, e.g., V(III), Cr(III), etc.

Source compounds for the neutral donor group(s) L include any neutral Lewis base compound(s) capable of donating an electron pair to the metal center. Non-limiting examples include diethyl ether, trimethylamine, tetrahydrofuran, dimethylaniline, aniline, trimethylphosphine, n-butylamine, and the like.

The bridging group T contains any element or group of elements from Groups 13–16 such as, for example, B, C, N, O, Al, Si, P, S, Ge, Se or the like. T may be saturated or unsaturated. Preferred bridging groups include dialkyl, alkylaryl or diaryl silicon radical; a dialkyl, alkylaryl or diaryl germanium radical; alkyl or aryl phosphine; alkyl or aryl amine radical; an oxygen or sulfur radical; or a dihydrocarbyl radical having 1 or more carbon atoms such as methylene, ethylene and the like. Specific, nonlimiting examples of the T group which are suitable are dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, di(p-t-butylphenethylsilyl), n-hexylmethylsilyl, cyclopentamethylenesilyl, cyclotetramethylenesilyl, cyclotrimethylenesilyl, dimethylgermanyl, diethylgermanyl, methylene, dimethylmethylene, diethylmethylene, ethylene, dimethylethylene, diethylethylene, dipropylethylene, propylene, dimethylpropylene, diethylpropylene, 1,1-dimethyl-3,3-dimethylpropylene, tetramethyldisiloxane, 1,1,4,4-tetramethyl-disilylethylene, oxygen and sulfur.

Exemplary hydrocarbyl radicals for X are methyl, ethyl, propyl, isopropyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for X include chlorine, bromine, fluorine and iodine, with chlorine being preferred. Exemplary alkoxides and aryloxides for X are methoxide, ethoxide, propoxide, butoxide, phenoxide and substituted phenoxides such as 4-methylphenoxide. Exemplary amides of X are dimethylamide, diethylamide, methylethylamide, di-t-butylamide, diisopropylamide and the like. Exemplary aryl amides are diphenylamide and other substituted phenyl amides. Exemplary silyl amides are di-trimethylsilylamide, di-triethylsilylamide and triethyltrimethyl silylamide, with di-trimethylsilylamide being preferred. Exemplary phosphides of X are diphenylphosphide, dicyclohexylphosphide, diethylphosphide, dimethylphosphide and the like. Exemplary alkylidene radicals for both X's together are methylene, ethylidene, propylidene, or the dianion of ethyleneglycol and the like.

Suitable hydrocarbyl and substituted hydrocarbyl radicals for the R groups will contain from 1 to about 30 carbon atoms and include singly and multiply branched alkyl radicals, cyclic hydrocarbon radicals, alkyl-substituted cyclic hydrocarbon radicals, aryl-substituted cyclic hydrocarbon radicals, aromatic radicals and alkyl-substituted aromatic radicals, amido-substituted hydrocarbon radicals, phosphido-substituted hydrocarbon radicals, alkoxy-substituted hydrocarbon radicals, and halo-substituted hydrocarbon radicals or hydrocarbon radicals containing substitutions by any Lewis basic or acidic functional group. Suitable organometallic radicals for the R group include trimethylsilyl, triphenylsilyl, triphenylgermyl, trimethylgermyl and the like. Other suitable radicals for the R group include amido radicals, phosphido radicals, alkoxy radicals, alkyl boride radicals and the like. Of the suitable organometallic R groups the radicals of silicon such as trimethylsilyl, triethylsilyl, ethyldimethylsilyl and methyldiethylsilyl are preferred; the most preferred being trimethylsilyl.

| | |
|---|---|
| [(Me$_2$PCH$_2$SiMe$_2$)$_2$N]TiCl$_2$ | [(Et$_2$PCH$_2$CH$_2$CH$_2$)$_2$N]FeEt$_2$ |
| [(Me$_2$PCH$_2$SiEt$_2$)$_2$N]VMe$_2$ | [(EtOCH$_2$CH$_2$)$_2$N]CoI$_2$ |
| [(MeOCH$_2$SiMe$_2$)$_2$N]CrBr$_2$ | [(EtN=CHCH$_2$)$_2$N]TiCl$_2$ |
| [(Et$_2$PCH$_2$SiMe$_2$)$_2$P]MnCl$_2$ | [(Ph$_2$NCH$_2$CH$_2$)$_2$N]VH$_2$ |
| [(Et$_2$CH$_2$SiEt$_2$)$_2$P]FeMe$_2$ | [(Ph$_2$NCH$_2$CH$_2$CH$_2$)$_2$N]CrMe$_2$ |
| [(MeN=CHSiMe$_2$)$_2$N]Co(CH$_2$CHCH$_2$)$_2$ | [(PhOCH$_2$CH$_2$)$_2$N]MnEt$_2$ |
| [(Ph$_2$PCH$_2$SiMe$_2$)$_2$N]TiCl$_2$ | [(PhN=CHCH$_2$)$_2$N]FeCl$_2$ |
| [(Ph$_2$PCH$_2$SiEt$_2$)$_2$N]VBr$_2$ | [(Me$_2$PSiMe$_2$)$_2$C$_6$H$_3$]TiCl$_2$ |
| [(PhN=CHSiMe$_2$)$_2$N]CrMe$_2$ | [(Me$_2$NCH$_2$)$_2$C$_6$H$_3$]VBr$_2$ |
| [(Me$_2$NCH$_2$CH$_2$)$_2$N]MnEt$_2$ | [(MeSCH$_2$)$_2$C$_6$H$_3$]CrMe$_2$ |
| [((Me$_3$Si)$_2$NCH$_2$CH$_2$)$_2$N]FeBr$_2$ | [(MeN=CH)$_2$C$_6$H$_3$]MnEt$_2$ |
| [(Me$_2$PCH$_2$CH$_2$CH$_2$)$_2$N]CoPh$_2$ | [(Et$_2$NCH$_2$)$_2$C$_6$H$_3$]FeCl$_2$ |
| [(MeN=CHCH$_2$)$_2$N]Ti(OMe)$_2$ | [(Et$_2$PSiMe$_2$)$_2$C$_6$H$_3$]Co(CH$_2$Ph)$_2$ |
| [(Et$_2$NCH$_2$CH$_2$)$_2$N]VCl$_2$ | [(Ph$_2$NCH$_2$)$_2$C$_6$H$_3$]Ti(NMe)$_2$ |
| [(Et$_2$NCH$_2$CH$_2$)$_2$P]CrBr$_2$ | [(PhOCH$_2$)$_2$C$_6$H$_3$]VPh$_2$ |
| [(Et$_2$NCH$_2$CH$_2$CH$_2$)$_2$N]MnMe$_2$ | [Ph$_2$PSiEt$_2$)$_2$C$_6$H$_3$]CrMe$_2$ |
| | [(PhN=CH)$_2$C$_6$H$_3$]FeCl$_2$, | and those illustrated in the examples that follow, where Ph=phenyl, Et=ethyl and Me=methyl.

The metal compounds according to the invention may be activated for coordination or insertion polymerization catalysis by known methods for either of Ziegler-Natta or metallocene transition metal compounds suitable for olefin polymerization. This activation is achieved for coordination polymerization by the inclusion of at least one ligand having a reactive metal-ligand sigma bond and at least one single vacant orbital adjacent (cis) to the sigma bound ligand, as is achieved by activation. The traditional activators of coordination polymerization art are suitable, those typically include Lewis acids such as Ziegler organometallic cocatalysts and alumoxane compounds, and ionizing, anion precursor compounds that abstract one ligand so as to ionize the metal center into a cationic complex and provide a counterbalancing weakly or noncoordinating anion.

The Ziegler cocatalyst will typically be an organometallic compound of a metal of Groups 1, 2, 12 or 13 of the Periodic Table of Elements. Preferred are organoaluminum compounds selected from the group consisting of aluminum alkyl and aluminum alkyl halide. These can be represented by the formulae:

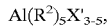

wherein $R^2$ is independently a hydride or $C_1$ to $C_{10}$ hydrocarbyl radicals including aliphatic, alicyclic or aromatic hydrocarbon radicals, X' is a halogen and s is an integer from 1 to 3; and,

which are hydrocarbylaluminum sesqui-halides. Examples include triethylaluminum, triisobutyl-aluminum, diethyl aluminumchloride, $Al_2Et_3Cl_3$ and $Al_2(i-Bu)_3Cl_3$.

Alkylalumoxanes and modified alkylalumoxanes are suitable as catalyst activators, particularly for the invention metal compounds comprising halide ligands. The alumoxane component useful as catalyst activator typically is an oligomeric aluminum compound represented by the general formula $(R''-Al-O)_n$, which is a cyclic compound, or $R''(R''-Al-O)_nAlR''_2$, which is a linear compound. In the general alumoxane formula R" is independently a $C_1$ to $C_{10}$ alkyl radical, for example, methyl, ethyl, propyl, butyl or pentyl and n is an integer from 1 to about 50. Most preferably, R" is methyl and n is at least 4. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a mixture of the linear and cyclic species of the alumoxane. Methylalumoxane and modified methylalumoxanes are preferred. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180, each being incorporated by reference for purposes of U.S. patent practice.

When the activator is an alumoxane, the preferred transition metal compound to activator molar ratio is from 1:2000 to 10:1, more preferably from about 1:500 to 10:1, even more preferably from about 1:250 to 1:1.

The term "noncoordinating anion" is recognized to mean an anion which either does not coordinate to the metal cation or which is only weakly coordinated to it thereby remaining sufficiently labile to be displaced by a neutral Lewis base, such as an olefinically or acetylenically unsaturated monomer.

Descriptions of ionic catalysts, those comprising a transition metal cationic complex and a noncoordinating anion, suitable for coordination polymerization appear in the early work in U.S. Pat. Nos. 5,064,802, 5,132,380, 5,198,401, 5,278,119, 5,321,106, 5,347,024, 5,408,017, 5,599,671, and WO 92/00333 and WO 93/14132. These teach a preferred method of preparation wherein metallocenes are protonated by noncoordinating anion precursors such that an alkyl/hydride group is abstracted by protonation from a transition metal to make it both cationic and charge-balanced by the noncoordinating anion. Since the abstraction and insertion ligands of such metallocenes also may be ligands of the metal compounds of the invention, similar methods of preparation as active polymerization catalyst components may be followed.

The use of ionizing ionic compounds not containing an active proton but capable of producing both an active metal cationic complex and a noncoordinating anion is also possible. See, EP-A-0 426 637, EP-A-0 573 403 and U.S. Pat. No. 5,387,568 for instructive ionic compounds. Reactive cations of the ionizing ionic compounds, other than the Bronsted acids, include ferrocenium, silver, tropylium, triphenylcarbenium and triethylsilylium, or alkali metal or alkaline earth metal cations such as sodium, magnesium or lithium cations. A further class of noncoordinating anion precursors suitable in accordance with this invention are hydrated salts comprising the alkali metal or alkaline earth metal cations and a non-coordinating anion as described above. The hydrated salts can be prepared by reaction of the metal cation-noncoordinating anion salt with water, for example, by hydrolysis of the commercially available or readily synthesized $LiB(pfp)_4$ which yields $[Li_xH_2O][B(pfp)_4]$, where (pfp) is pentafluorophenyl or perfluorophenyl.

Any metal or metalloid capable of forming a coordination complex which is resistant to degradation by water (or other Bronsted or Lewis Acids) may be used or contained in the noncoordinating anion. Suitable metals include, but are not limited to, aluminum, gold, platinum and the like. Suitable metalloids include, but are not limited to, boron, phosphorus, silicon and the like. The description of noncoordinating anions and precursors thereto of the documents of the foregoing paragraphs are incorporated by reference for purposes of U.S. patent practice.

An additional method of making the active polymerization catalysts of this invention uses ionizing anion precursors which are initially neutral Lewis acids but form a metal cationic complex and the noncoordinating anion upon ionizing reaction with the invention compounds, for example tris(pentafluorophenyl) boron acts to abstract a hydrocarbyl, hydride or silyl ligand to yield an invention metal cationic complex and stabilizing noncoordinating anion, see EP-A-0 427 697 and EP-A-0 520 732 for illustration utilizing Group 4 metallocene compounds. See also the methods and compounds of EP-A-0 495 375. The description of noncoordinating anions and precursors thereto of these documents are similarly incorporated by reference for purposes of U.S. patent practice.

When the cation portion of an ionic noncoordinating anion precursor is a Bronsted acid such as protons or protonated Lewis bases (excluding water), or a reducible Lewis acid such as ferrocenium or silver cations, or alkaline metal or alkaline earth metal cations such as those of sodium, magnesium or lithium cations, the transition metal to activator molar ratio may be any ratio, but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred.

The catalyst complexes of the invention are useful in polymerization of unsaturated monomers conventionally known to be polymerizable under coordination polymerization conditions using metallocenes. Such conditions are well known and include solution polymerization, slurry polymerization, gas-phase polymerization, and high pressure polymerization. The catalyst of the invention may be supported and as such will be particularly useful in the known operating modes employing fixed-bed, moving-bed, fluid-bed, slurry or solution processes conducted in single, series or parallel reactors.

When using the catalysts of the invention, particularly when immobilized on a support, the total catalyst system will generally additionally comprise one or more scavenging compounds. The term "scavenging compounds" as used in this application and its claims is meant to include those compounds effective for removing polar impurities from the reaction environment. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion precursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be used in the polymerization process itself.

Typically the scavenging compound will be an organometallic compound such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and n-octyl aluminum. Those scavenging compounds having bulky or $C_6$–$C_{20}$ linear hydrocarbyl substituents covalently bound to the metal or metalloid center are preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present will act as scavenger compounds and additional scavenging compounds may not be necessary. Alumoxanes also may be used in scavenging amounts with other means of activation, e.g., methylalumoxane and triisobutyl-aluminoxane. The amount of scavenging agent to be used with Group 4–9 catalyst compounds of the invention is minimized during polymerization reactions to that amount effective to enhance activity and avoided altogether if the feeds can be sufficiently free of adventitious impurities.

The catalyst according to the invention may be supported for use in gas phase, bulk, slurry polymerization processes, or otherwise as needed. Numerous methods of support are known in the art for copolymerization processes for olefins, particularly for catalysts activated by alumoxanes. Any is suitable for the invention process in its broadest scope. See, for example, U.S. Pat. Nos. 5,057,475 and 5,227,440. An example of supported ionic catalysts appears in WO 94/03056. A particularly effective method is that described in U.S. Pat. No. 5,643,847, and WO 96/04319. A bulk, or slurry, process utilizing supported, invention Group 4–9 metal compounds activated with alumoxane co-catalysts can be utilized as described for ethylene-propylene rubber in U.S. Pat. Nos. 5.,001,205 and 5,229,478, these processes will additionally be suitable with the catalyst systems of this application. Thus both inorganic oxide and polymeric particulate supports may be utilized in accordance with the knowledge in the field. See additionally, U.S. Pat. Nos. 5,422,325, 5,427,991, 5,498,582 and 5,466,649, and international publications WO 93/11172 and WO 94/07928. Each of the foregoing documents is incorporated by reference for purposes of U.S. patent practice.

In preferred embodiments of the process for this invention, the catalyst system is employed in liquid phase (solution, slurry, suspension, bulk phase or combinations thereof), in high pressure liquid or supercritical fluid phase, or in gas phase. Each of these processes may be employed in singular, parallel or series reactors. The liquid processes comprise contacting olefin monomers with the above described catalyst system in a suitable diluent or solvent and allowing said monomers to react for a sufficient time to produce the invention copolymers. Hydrocarbyl solvents are suitable, both aliphatic and aromatic, hexane and toluene are preferred. Halocarbon solvents, e.g., methylene chloride will additionally be suitable. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5352, 749, 5,436,304, 5,453,471, and 5,463,999, and WO 95/07942. Each is incorporated by reference for purposes of U.S. patent practice.

Generally speaking the polymerization reaction temperature can vary from about –50° C. to about 250° C. Preferably the reaction temperature conditions will be from –20° C. to 220°, more preferably below 200° C. The pressure can vary from about 1 mm Hg to 2500 bar, preferably from 0.1 bar to 1600 bar, most preferably from 1.0 to 500 bar. Where lower molecular weight copolymers, e.g., Mn<10,000, are sought it will be suitable to conduct the reaction processes at temperatures above about 0° C. and pressures under 500 bar. The multiboron activators of U.S. Pat. No. 5,278,119 can additionally be employed to facilitate the preparation of the low molecular weight copolymers of the invention.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, diolefins or cyclic olefins, are produced by adding ethylene, and optionally one or more of the other monomers, to a reaction vessel under low pressure (typically<50 bar), at a typical temperature of 20–250° C. with the invention catalyst that has been slurried with a solvent, such as hexane or toluene. Heat of polymerization is typically removed by cooling. Gas phase polymerization can be conducted, for example, in a continuous fluid bed gas-phase reactor operated at 2000–3000 kPa and 60–160 °

C., using hydrogen as a reaction modifier (100–200 ppm), $C_4$–$C_8$, comonomer feedstream (0.5–1.2 mol%), and $C_2$ feedstream (25–35 mol%). See, U.S. Pat. Nos. 4,543,399, 4,588,790, 5,028,670 and 5,405,922 and 5,462,999, which are incorporated by reference for purposes of U.S. patent practice.

Ethylene-α--olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between −10–160° C. The process can be carried out in a stirred tank reactor, or more than one operated in series or parallel. See the general disclosure of U.S. Pat. No. 5,001,205, WO 96/33,227 and WO 97/22,639 which are incorporated by reference for their description of polymerization processes, ionic activators and useful scavenging compounds.

Pre-polymerization of the supported catalyst of the invention may also be used for further control of polymer particle morphology in typical slurry or gas phase reaction processes in accordance with conventional teachings. For example, such can be accomplished by pre-polymerizing a $C_2$–$C_6$ alpha-olefin for a limited time, for example, ethylene is contacted with the supported catalyst at a temperature of −15° to 30° C. and ethylene pressure of up to about 250 psig (1724 kPa) for 75 min to obtain a polymeric coating on the support of polyethylene of 30,000–150,000 molecular weight. The pre-polymerized catalyst is then available for use in the polymerization processes referred to above. The use of polymeric resins as a support coating may additionally be utilized, typically by suspending a solid support in dissolved resin of such material as polystyrene with subsequent separation and drying.

Other olefinically unsaturated monomers besides those specifically described above may be polymerized using the catalysts according to the invention, for example, styrene, alkyl-substituted styrene, ethylidene norbornene, norbornadiene, dicyclopentadiene, and other olefinically-unsaturated monomers, including other cyclic olefins, such as cyclopentene, norbornene, and alkyl-substituted norbornenes. Additionally, alpha-olefinic macromonomers of up to 100 mer units, or more, may also be incorporated by copolymerization.

The catalyst compositions of the invention can be used as described above individually for coordination polymerization or can be mixed to prepare polymer blends with other known olefin polymerization catalyst compounds. By use of mixtures, of coordination catalyst compounds, polymer blends can be prepared under polymerization conditions analogous to those using individual catalyst compositions. Polymers having increased molecular weight distribution ("MWD") for improved processing and other traditional benefits available from polymers made with mixed catalyst systems can thus be achieved.

EXAMPLES

The following examples are presented to illustrate the foregoing discussion. All parts, proportions, and percentages are by weight unless otherwise indicated. All reactions and manipulations have been conducted using dry, oxygen-free solvents under an inert nitrogen atmosphere. Although the examples may be directed toward certain embodiments of the present invention, they are not to be viewed as limiting the invention in any specific respect. In these examples, certain abbreviations are used to facilitate the description. These include standard chemical abbreviations for the elements and certain commonly accepted abbreviations, such as: Me=methyl, Et=ethyl, Bu=butyl, Ph=phenyl, and thf=tetrahydrofuran. Abbreviations used in the accompanying tables include Cat=catalyst, T=temperature, P=pressure, t=time, TM=transition metal and Br=branches per 1000 C atoms.

All molecular weights are weight average molecular weight unless otherwise noted. Molecular weights (weight average molecular weight ($M_w$) and number average molecular weight ($M_n$) were measured by Gel Permeation Chromatography, unless otherwise noted, using a Waters 150 Gel Permeation Chromatograph equipped with a differential refractive index detector and calibrated using polystyrene standards. Samples were run in either THF (45° C.) or in 1,2,4-trichlorobenzene (145° C.) depending upon the sample's solubility using three Shodex GPC AT-80 M/S columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.1 units for $M_w/M_n$ which was calculated from elution times. The numerical analyses were performed using Expert Ease® software available from Waters Corporation.

Example 1

Synthesis of $[(Ph_2PCH_2SiMe_2)_2N]TiCl_2$ (1)

To a solution of $(Ph_2PCH_2SiMe_2)_2NH$ (0.500 g, 0.944 mmol) in pentane (15 mL) was added a 1.6 M solution of BuLi in hexanes (0.59 mL, 0.94 mmol). Upon addition, a white precipitate formed and the mixture was stirred at room temperature for 30 min. The solid was allowed to settle and the solvent was removed by pipette. The solid was washed with pentane (10 mL) and then dissolved in thf(10 mL). The thf solution was added dropwise to a suspension of $TiCl_3$.3thf (0.350 g, 0.944 mmol) in thf (30 mL). Upon addition, the color changed from light blue to olive green. After stirring at room temperature for 16 h, the volatiles were removed under reduced pressure and the residue was extracted with toluene (30 mL). The deep green solution was filtered through Celite®, concentrated to 10 mL, and cooled to −30° C. The product was isolated as lime green crystals (0.291 g, 0.449 mmol, 48%). The elemental analysis, IR spectrum, and magnetic moment were consistent with the title compound.

Example 2

Synthesis of $[(Ph_2PCH_2SiMe_2)_2N]VCl_2$ (2)

This compound was synthesized as described for the Ti derivative in Example 1 from $VCl_3$.3thf (0.353 g, 0.944 mmol) and $(Ph_2PCH_2SiMe_2)_2NH$ (0.500 g, 0.944 mmol). The product was isolated as deep red crystals from toluene/pentane. The yield was 0.415 g (0.638 mmol, 68%). The elemental analysis, IR spectrum, magnetic moment, and X-ray crystallographic data were consistent with the title compound.

Example 3

Synthesis of [(Ph$_2$PCH$_2$SiMe$_2$)$_2$N]CrCl$_2$(thf) (3)

This compound was synthesized as described for the Ti derivative in Example 1 from CrCl$_3$.3thf (0.707 g, 1.89 mmol) and (Ph$_2$PCH$_2$SiMe$_2$)$_2$NH (1.00 g, 1.89 mmol). The product was isolated as magenta microcrystals from toluene/pentane. One molecule of thf was coordinated to the metal. The yield was 0.644 g (0.890 mmol, 47%). The elemental analysis, IR spectrum, magnetic moment, and X-ray crystallographic data were consistent with the title compound.

Example 4

Synthesis of [(Ph$_2$PCH$_2$SiMe$_2$)$_2$N]FeCl$_2$ (4)

This compound was synthesized as described for the Ti derivative in Example 1 from FeCl$_3$ (0.153 g, 0.944 mmol) and (Ph$_2$PCH$_2$SiMe$_2$)$_2$NH (0.500 g, 0.944 mmol). The product was isolated as dark green-brown crystals from toluene/pentane. The yield was 0.383 g (0.584 mmol, 62%). The elemental analysis, IR spectrum, and magnetic moment were consistent with the title compound.

Example 5 (Comparative)

Synthesis of [(Et$_2$NCH$_2$CH$_2$)$_2$N]ScCl$_2$ (5)

A solution of (Et$_2$NCH$_2$CH$_2$)$_2$NLi (0.731 g, 3.30 mmol) in thf (7 mL) was added dropwise to a suspension of ScCl$_3$ (0.500g, 3.30 mmol) in thf (30 mL) at −78° C. After addition, the mixture was slowly warmed to room temperature and stirred for 18 h. The volatiles were removed under reduced pressure and the residue was extracted with pentane (80 mL). The solution was filtered through Celite® and cooled to −25° C. The product was isolated as white, blocky crystals (0244 g, 0.739 mmol, 22%). The elemental analysis and $^1$H NMR spectrum were consistent with the title compound.

Examples 6–7

Synthesis of [(Et$_2$NCH$_2$CH$_2$)N]TiCl$_2$ (6) and [(Et$_2$NCH$_2$CH$_2$CH$_2$)N]VCl$_2$ (7)

The title compounds were synthesized as described in Wills et al., *J. Chem.Soc., Dalton Trans.*, p. 1253 (1989).

Example 8

Synthesis of [(Et$_2$NCH$_2$CH$_2$)$_2$N]CrCl$_2$ (8)

This compound was synthesized as described for the Sc derivative of Example 5 from CrCl$_3$.3thf (1.69 g, 4.52 mmol) and (Et$_2$NCH$_2$CH$_2$)$_2$NLi (1.00 g, 4.52 mmol) except that the reaction was stirred at room temperature for 3 h and the product was crystallized from pentane/toluene. The product was isolated as dark, green-brown crystals (0.528 g, 1.57 mmol, 35%). The elemental analysis, IR spectrum, and magnetic moment were consistent with the title compound.

Example 9

Synthesis of [(Me$_2$NCH$_2$)$_2$C$_6$H$_3$]VCl$_2$ (9)

A solution of (Me$_2$NCH$_2$)$_2$C$_6$H$_3$Li (0.500 g, 2.52 mmol) in benzene (10 mL) was added dropwise to a suspension of VCl$_3$.3thf (0.943 g, 2.52 mmol) in benzene (40 mL). Upon addition, the solids dissolved leaving a deep red solution. After stirring at room temperature for 18 h, the solution was filtered through Celite® and concentrated to 20 mL. The solution was diluted with pentane (20 mL) and filtered. The solution was cooled to −30° C. resulting in the formation of a mass of red needles and partial crystallization of the benzene. The mixture was warmed until the benzene just melted and the crystalline product was collected. The yield of product was 0.287 (0.916 mmol, 36%). The elemental analysis, IR spectrum, and magnetic moment were consistent with the title compound.

Example 10

Synthesis of [(Me$_2$NCH$_2$)$_2$C$_6$H$_3$]CrCl$_2$ (10)

This compound was synthesized as described for the V derivative of Example 9 from CrCl$_3$.3thf (0.453 g, 1.21 mmol) and (Me$_2$NCH$_2$)$_2$C$_6$H$_3$Li (0.240 g, 1.21 mmol). The product was isolated as green microcrystals (0.152 g, 0.484 mmol, 40%). The elemental analysis, IR spectrum, and magnetic moment were consistent with the title compound.

Examples 11

Synthesis of [(Me$_2$NCH$_2$)$_2$C$_6$H$_3$]FeCl$_2$ (11)

The title compound was synthesized as described in Kanters, et al., *Acta. Cryst.*, vol. C41, p. 893 (1985).

Examples 12–13

Synthesis of [(Et$_2$NCH$_2$CH$_2$)$_2$N]TiMe$_2$ (12) and [Et$_2$NCH$_2$CH$_2$)$_2$N]VMe$_2$ (13)

The title compounds were prepared as described in Wills et al., *J. Chem. Soc., Dalton Trans.*, p. 1253 (1989).

Examples 14–54

Ethylene Homopolymerization Method (MAO Activation)

Polymerizations were performed in a hot, nitrogen purged 500 mL Zipperclave reactor (Autoclave Engineers) in dry hexane (250 mL) as the polymerization solvent/diluent. The catalyst was activated with methylalumoxane (MAO) in a 10 wt % toluene solution (Albemarle) unless otherwise noted. Usually, 2.5 mL of the MAO solution was diluted with fresh toluene prior to injection into the hexane-filled reactor. The hexane in the reactor was then saturated with ethylene at the designated pressure and temperature. The catalyst solution was prepared in the drybox by mixing from 5 to 50 mg of catalyst precursor with toluene (50 mL). The catalyst precursor solution was pumped to the reactor, and combined with the previously added cocatalyst solution, until the ethylene make-up flow became constant during the polymerization. The reactor temperature was controlled by a steam/water mixture flowing through the reactor jacket. The polymerizations were run for 30 min. At the end of the run, the ethylene was vented and the reactor was cooled down. The reactor contents were poured into a 1 L beaker and treated with isopropyl alcohol or acetone. The polymer solvent mixture was blown down with nitrogen or filtered to recover the polymer. The final product was dried under vacuum at 60 to 90° C. for about 12 h. The polymerization conditions and results are shown in Table 1.

TABLE 1

| Example | Cat. | T (° C.) | P (psi) | t (min) | TM (μmol) | Al:TM | Yield (g) | gPE mmolTM.h | $M_w$(k) | MWD |
|---|---|---|---|---|---|---|---|---|---|---|
| 14 | 1 | 30 | 76 | 30 | 25.6 | 149 | 2.2 | 169 | 506 | 2.4 |
| 15 | 1 | 60 | 125 | 30 | 9.6 | 400 | 2.9 | 612 | 244 | 77 |
| 16 | 1 | 115 | 275 | 30 | 9.6 | 400 | 3.6 | 758 | 33 | 22 |
| 17 | 1 | 140 | 375 | 30 | 24.7 | 155 | 4.0 | 325 | 16 | 11 |
| 18 | 2 | 30 | 75 | 30 | 0.6 | 6079 | 0.6 | 1809 | 1437 | 2.6 |
| 19 | 2 | 60 | 125 | 30 | 1.1 | 3367 | 1.2 | 2145 | 1136 | 2.5 |
| 20 | 2 | 115 | 276 | 30 | 5.9 | 649 | 1.1 | 386 | 135 | 159 |
| 21 | 2 | 140 | 350 | 30 | 21.2 | 180 | 0.9 | 88 | 75 | 89 |
| 22 | 3 | 30 | 75 | 30 | 2.2 | 1733 | 2.8 | 2569 | 448 | 16 |
| 23 | 3 | 60 | 125 | 30 | 8.6 | 447 | 4.0 | 934 | 134 | 2.9 |
| 24 | 3 | 115 | 275 | 30 | 8.4 | 454 | 8.2 | 1936 | 53 | 2.2 |
| 25 | 3 | 140 | 351 | 30 | 12.1 | 318 | 0.4 | 66 | 42 | 7.2 |
| 26 | 4 | 30 | 75 | 30 | 44.9 | 171 | 0.5 | 22 | NM | NM |
| 27 | 4 | 60 | 125 | 30 | 43.9 | 174 | 0.6 | 27 | NM | NM |
| 28 | 4 | 115 | 275 | 30 | 44.9 | 171 | 0.7 | 29 | NM | NM |
| 29 | 5 | 30 | 75 | 30 | 30.2 | 127 | 0.4 | 23 | NM | NM |
| 30 | 5 | 60 | 125 | 30 | 60.5 | 63 | 0.5 | 15 | NM | NM |
| 31 | 5 | 115 | 275 | 30 | 95.2 | 40 | 0.3 | 6 | NM | NM |
| 32 | 5 | 140 | 350 | 30 | 82.0 | 47 | 1.2 | 29 | 182 | 54 |
| 33 | 6 | 30 | 75 | 30 | 87.3 | 44 | 0.3 | 6 | NM | NM |
| 34 | 6 | 60 | 125 | 30 | 88.2 | 43 | 1.3 | 29 | 504 | 6.4 |
| 35 | 6 | 115 | 275 | 30 | 11.3 | 338 | 7.6 | 1345 | 190 | 11 |
| 36 | 6 | 140 | 350 | 30 | 49.8 | 77 | 11.0 | 442 | 278 | 6.2 |
| 37 | 7 | 30 | 75 | 30 | 83.0 | 46 | 0.7 | 17 | NM | NM |
| 38 | 7 | 60 | 125 | 30 | 86.6 | 44 | 1.7 | 39 | 177 | 27 |
| 39 | 7 | 115 | 275 | 30 | 47.3 | 81 | 7.9 | 332 | 59 | 4.0 |
| 40 | 7 | 140 | 350 | 30 | 57.1 | 67 | 11.6 | 406 | 53 | 2.9 |
| 41 | 8 | 30 | 75 | 30 | 85.3 | 90 | 0.6 | 15 | NM | NM |
| 42 | 8 | 60 | 125 | 30 | 87.2 | 88 | 0.5 | 12 | NM | NM |
| 43 | 8 | 115 | 275 | 30 | 85.4 | 90 | 0.7 | 17 | NM | NM |
| 44 | 9 | 30 | 75 | 30 | 20.1 | 190 | 4.7 | 468 | NM | NM |
| 45 | 9 | 60 | 125 | 30 | 21.1 | 182 | 3.3 | 313 | NM | NM |
| 46 | 9 | 115 | 275 | 30 | 10.5 | 364 | 0.8 | 142 | NM | NM |
| 47 | 9 | 140 | 350 | 30 | 84.3 | 45 | 0.8 | 19 | NM | NM |
| 48 | 10 | 30 | 75 | 30 | 61.1 | 125 | 0.8 | 26 | NM | NM |
| 49 | 10 | 60 | 125 | 30 | 91.7 | 84 | 0.9 | 19 | NM | NM |
| 50 | 10 | 115 | 275 | 30 | 91.7 | 84 | 0.6 | 14 | NM | NM |
| 51 | 10 | 140 | 350 | 30 | 91.7 | 84 | 0.9 | 20 | NM | NM |
| 52 | 11 | 30 | 75 | 30 | 86.8 | 88 | 0.5 | 11 | NM | NM |
| 53 | 11 | 60 | 125 | 30 | 90.5 | 85 | 0.7 | 15 | NM | NM |
| 54 | 11 | 115 | 275 | 30 | 90.5 | 85 | 0.9 | 19 | NM | NM |

NM-not measured

Examples 55–59

Propylene Homopolymerization Method (MAO Activation)

Polymerizations were performed in a hot, nitrogen purged 500 mL Zipperclave reactor (Autoclave Engineers). The catalyst was activated with methylalumoxane (MAO) in a 10 wt % toluene solution (Albemarle) unless otherwise noted. Usually, 2.5 mL of the MAO solution was diluted with fresh toluene prior to injection into the reactor. Liquid propylene (300 mL) was then added to the reactor at room temperature and the contents were heated to the desired polymerization temperature. The catalyst solution was prepared in the drybox by mixing from 5 to 50 mg of catalyst precursor with toluene (50 mL). The catalyst precursor solution was pumped to the reactor, and combined with the previously added cocatalyst solution, until the reactor temperature and pressure became constant during the polymerization. The reactor temperature was controlled by a steam/water mixture flowing through the reactor jacket. The polymerizations were run for 30 min. At the end of the run, the propylene was vented and the reactor was cooled down. The reactor contents were rinsed into a 1 L beaker with hexane or toluene and treated with isopropyl alcohol or acetone. The polymer solvent mixture was blown down with nitrogen or filtered to recover the polymer. The final product was dried under vacuum at 60 to 90° C. for about 12 h. The polymerization conditions and results are shown in Table 2.

TABLE 2

| Example | Cat. | T (° C.) | $C_3$(mL) | t (min) | μmol TM | Al:TM | Yield(g) | gPP/mmolTM.h |
|---|---|---|---|---|---|---|---|---|
| 55 | 3 | 60 | 300 | 30 | 1.1 | 3466 | 0.3 | 615 |
| 56 | 4 | 60 | 300 | 30 | 43.9 | 174 | 1.0 | 46 |
| 57 | 5 | 60 | 300 | 30 | 84.1 | 46 | 0.3 | 7 |
| 58 | 8 | 60 | 300 | 30 | 85.4 | 90 | 1.1 | 25 |
| 59 | 10 | 60 | 300 | 30 | 100.9 | 76 | 0.9 | 17 |

Examples 60–72

Ethylene/1-hexene Copolymerization Method (MAO Activation)

The ethylene/1-hexene copolymerizations were run as previously described for the ethylene homopolymerizations except that 1-hexene was added to the reactor immediately prior to the addition of the MAO. The polymerization conditions and results are shown in Table 3 and the polymer characterization for selected samples is shown in Table 4.

TABLE 3

| Example | Cat. | T(° C.) | P $C_2^=$ (psi) | $C_6^=$ (mL) | t (min) | TM ($\mu$mol) | Al:TM | Yield (g) | gEH mmolTM.h |
|---|---|---|---|---|---|---|---|---|---|
| 60 | 1 | 60 | 60 | 15 | 30 | 11.1 | 345 | 4.1 | 736 |
| 61 | 2 | 60 | 60 | 15 | 30 | 45.7 | 84 | 0.9 | 40 |
| 62 | 3 | 60 | 61 | 15 | 30 | 4.4 | 866 | 4.3 | 1922 |
| 63 | 4 | 60 | 60 | 15 | 30 | 43.9 | 174 | 0.6 | 25 |
| 64 | 5 | 60 | 60 | 15 | 30 | 91.7 | 42 | 0.2 | 5 |
| 65 | 6 | 60 | 60 | 15 | 30 | 85.5 | 45 | 0.5 | 11 |
| 66 | 6 | 115 | 115 | 15 | 30 | 14.4 | 532 | 8.9 | 1231 |
| 67 | 7 | 60 | 60 | 15 | 30 | 86.6 | 44 | 0.3 | 7 |
| 68 | 7 | 115 | 275 | 15 | 30 | 73.2 | 105 | 3.0 | 81 |
| 69 | 8 | 60 | 60 | 15 | 30 | 85.4 | 90 | 0.7 | 16 |
| 70 | 9 | 60 | 60 | 15 | 30 | 93.9 | 41 | 0.9 | 19 |
| 71 | 10 | 60 | 60 | 15 | 30 | 84.0 | 91 | 0.5 | 13 |
| 72 | 11 | 60 | 60 | 15 | 30 | 90.5 | 85 | 0.7 | 15 |

TABLE 4

| Example | Cat. | $M_w$ (k) | MWD | Br |
|---|---|---|---|---|
| 60 | 1 | 65 | 2.0 | 2 |
| 62 | 3 | 68 | 1.8 | 1 |
| 66 | 6 | 75 | 8.3 | 5 |
| 68 | 7 | 49 | 12.0 | 8 |

Example 73

Ethylene/norbornene Copolymerization with [(Ph$_2$PCH$_2$SiMe$_2$)$_2$N] CrCl$_2$(thf) MAO Activation)

The ethylene/norbornene copolymerization was run as previously described for the ethylene homopolymerizations except that norbornene (22 mL of an 80 wt % solution in hexane) was added to the reactor immediately prior to the addition of the MAO. The polymerization was run at 60° C. with 61 psi ethylene using 3.6 mmols of [( Ph$_2$PCH$_2$SiMe$_2$)$_2$N]CrCl$_2$(thf) and an Al:TM ratio of 1075. The yield of copolymer was 2.6 g giving an activity of 1448 g ENB/mmol TM.h. The copolymer had Mw=647 k and MWD=2.9

Examples 74–81

Ethylene Homopolymerization Method ([Ph$_3$C][B(C$_6$F$_5$)$_4$] Activation)

Polymerizations were performed in a hot, nitrogen purged 500 mL Zipperclave reactor (Autoclave Engineers) in dry hexane (250 mL) as the polymerization solvent/diluent. To the diluent was added 0.2 mL of a 25 wt % solution of triisobutylaluminum in heptane (Akzo Nobel). The hexane in the reactor was then saturated with ethylene at the designated pressure and temperature. The catalyst solution was prepared in the drybox by mixing from 5 to 50 mg of catalyst precursor with an equimolar amount of [Ph$_3$C][B(C$_6$F$_5$)$_4$] in toluene (50 mL). The catalyst solution was pumped to the reactor until the ethylene make-up flow became constant during the polymerization. The reactor temperature was controlled by a steam/water mixture flowing through the reactor jacket. The polymerizations were run for 30 min. At the end of the run, the ethylene was vented and the reactor was cooled down. The reactor contents were poured into a 1 L beaker and treated with isopropyl alcohol or acetone. The polymer solvent mixture was blown down with nitrogen or filtered to recover the polymer. The final product was dried under vacuum at 60 to 90° C. for about 12 h. The polymerization conditions and results are own in Table 5.

TABLE 5

| Example | Cat. | T (° C.) | P (psi) | t (min) | TM ($\mu$mol) | Yield (g) | gPE/mmol TM.h | Mw(k) | MWD |
|---|---|---|---|---|---|---|---|---|---|
| 74 | 12 | 30 | 75 | 30 | 31.4 | 1.4 | 86 | 772 | 4.3 |
| 75 | 12 | 60 | 125 | 23 | 7.8 | 11.0 | 3679 | NM | NM |
| 76 | 12 | 115 | 275 | 30 | 7.2 | 7.4 | 2059 | NM | NM |
| 77 | 12 | 140 | 350 | 30 | 6.8 | 5.0 | 1463 | NM | NM |
| 78 | 13 | 32 | 75 | 30 | 29.2 | 0.1 | 4 | NM | NM |
| 79 | 13 | 60 | 125 | 30 | 28.4 | 0.3 | 18 | NM | NM |
| 80 | 13 | 115 | 275 | 30 | 65.7 | 3.3 | 100 | 241 | 3.5 |
| 81 | 13 | 140 | 350 | 30 | 38.3 | 0.8 | 41 | NM | NM |

Examples 82–83

Propylene Homopolymerization Method ([Ph$_3$C][B(C6F$_5$)$_4$] Activation)

Polymerizations were performed in a hot, nitrogen purged 500 mL Zipperclave reactor (Autoclave Engineers). To the reactor was added 0.2 mL of a 25 wt. % solution of triisobutylaluminum in heptane (Akzo Nobel). Liquid propylene (300 mL) was then added to the reactor at room temperature and the contents were heated to the desired polymerization temperature. The catalyst solution was prepared in the drybox by mixing from 5 to 50 mg of catalyst precursor with an equimolar amount of $[Ph_3C][B(C_6F_5)_4]$ in toluene (50 mL). The catalyst precursor solution was pumped to the reactor until the reactor temperature and pressure became constant during the polymerization. The reactor temperature was controlled by a steam/water mixture flowing through the reactor jacket. The polymerizations were run for 30 min. At the end of the run, the propylene was vented and the reactor was cooled down. The reactor contents were rinsed into a 1 L beaker with hexane or toluene and treated with isopropyl alcohol or acetone. The polymer solvent mixture was blown down with nitrogen or filtered to recover the polymer. The final product was dried under vacuum at 60 to 90° C. for about 12 h. The polymerization conditions and results are shown in Table 6.

TABLE 6

| Example | Cat. | T (° C.) | $C_3$ (mL) | t (min) | TM ($\mu$mol) | Yield (g) | gPP/mmol TM.h | Mw(k) | MWD |
|---|---|---|---|---|---|---|---|---|---|
| 82 | 12 | 60 | 300 | 30 | 33.8 | 6.6 | 387 | 394 | 6.5 |
| 83 | 13 | 60 | 300 | 30 | 33.5 | 0.6 | 35 | NM | NM |

Examples 84–87

Ethylene/1-hexene Copolymerization Method ($[Ph_3C][B(C_6F_5)_4]$ Activation)

The ethylene/1-hexene copolymerizations were run as previously described for the ethylene homopolymerizations with $[Ph_3C][B(C_6F_5)_4]$ activation except that 1-hexene was added to the reactor immediately prior to the addition of the triisobutylaluminum. The polymerization conditions and results are shown in Table 7.

TABLE 7

| Example | Cat. | T (° C.) | P $C_2^=$ (psi) | $C_6^=$ (mL) | t (min) | TM ($\mu$mol) | Yield (g) | gEH mmolTM.h | Mw (k) | MWD | Br |
|---|---|---|---|---|---|---|---|---|---|---|---|
| 84 | 12 | 60 | 60 | 15 | 30 | 12.2 | 5.1 | 829 | 549 | 2.6 | 34 |
| 85 | 12 | 115 | 150 | 15 | 30 | 11.6 | 4.6 | 785 | 157 | 4.0 | 12 |
| 86 | 13 | 60 | 60 | 15 | 30 | 59.9 | 0.1 | 3 | NM | NM | NM |
| 87 | 13 | 115 | 150 | 15 | 30 | 73.1 | 0.3 | 7 | NM | NM | NM |

The following is claimed:

1. A catalyst complex for coordination polymerization comprising a Group 4–9 first or second row transition metal complex in a reduced oxidation state having a monoanionic tridentate ancillary ligand system consisting of (a) two Group 15 or 16 atoms, wherein the two Group 15 or 16 atoms are datively bound to the metal and (b) a Group 15 atom or $\eta^1$-aromatic ring carbon atom
      (i) covalently bound to the metal and
      (ii) linked to the Group 15 or 16 atoms by bridging groups comprising Group 13–16 elements, wherein each bridging group links the covalently bound moiety to only one datively bound moiety.

2. The catalyst complex of claim 1 comprising the reaction product of:

(a) an organometallic complex of one of the formulae:

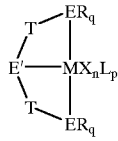
   (A)

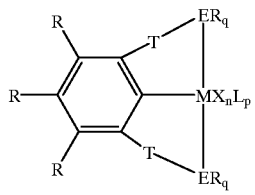
   (B)

wherein
   (i) M is a transition metal from Groups 4–9 in a reduced oxidation state;
   (ii) each X is independently halogen, alkoxide, aryloxide, amide, phosphide, hydride, hydrocarbyl, substituted hydrocarbyl, halocarbyl, substituted halocarbyl, hydrocarbyl- or halocarbyl-substituted organometalloid, or two X groups are joined and bound to the transition metal or an L group to form a ring structure, or one or more of X can contain an L group;
   (iii) L is a neutral donor group;
   (iv) R has the same definition as X;
   (v) E is independently a donor group selected from Groups 15 and 16;
   (vi) E' is a monoanionic donor group selected from Group 15;
   (vii) T is a bridging group comprising any element or combination of elements from Groups 13–16;
   (viii) n is a number from 1 to 3 which is determined by counterbalancing the charge on the metal such that the metal remains in a reduced oxidation state and the overall charge on the complex is neutral;
   (ix) p is a number from 0 to 3;
   (x) q is 1 or 2 such that E remains a neutral donor group; and (b) a catalyst activator compound.

3. The catalyst system of claim 2 wherein each E is independently N, P, S or O, and E' is N or P.

4. The catalyst system of claim 2 wherein M is in the +3 oxidation state and n is 2.

5. The catalyst system of claim 2 wherein M is selected from Ti, V, Cr, Mn, Fe or Co.

6. The catalyst system of claim 2 wherein the catalyst activator compound is an alkylalumoxane, an alkyl aluminum cocatalyst activator, or an ionizing noncoordinating anion precursor compound.

7. A polymerization process characterized by contacting one or more monomers polymerizable by coordination polymerization under suitable coordination polymerization conditions with a catalyst complex of claim 1.

8. A polymerization process characterized by contacting one or more monomers polymerizable by coordination polymerization under suitable coordination polymerization conditions with a catalyst complex of claim 2.

9. The process of claim 7 wherein said monomers are selected from the group consisting of ethylene, α-olefins, cyclic olefins, non-conjugated diolefins, acetylenically unsaturated monomers, olefinically unsaturated aromatic monomers and $C_{20}$–$C_{200}$ macromonomers.

10. The process of claim 9 wherein said monomers comprise at least one member selected from the group consisting of ethylene and $C_3$–$C_{20}$ α-olefins.

11. The process of claim 9 wherein said catalyst system comprises a solid particulate support.

12. The process of claim 8 wherein said monomers are selected from the group consisting of ethylene, α-olefins, cyclic olefins, non-conjugated diolefins, acetylenically unsaturated monomers, olefinically unsaturated aromatic monomers and $C_{20}$–$C_{200}$ macromonomers.

13. The process of claim 12 wherein said monomers comprise at least one member selected from the group consisting of ethylene and $C_3$–$C_{20}$ α-olefins.

14. The process of claim 12 wherein said catalyst system comprises a solid particulate support.

* * * * *

UNITED STATES PATENT AND TRADEMARK OFFICE
CERTIFICATE OF CORRECTION

PATENT NO. : 6,294,495 B1
DATED : September 25, 2001
INVENTOR(S) : Phillip T. Matsunaga Page 1 of 1

It is certified that error appears in the above-identified patent and that said Letters Patent is hereby corrected as shown below:

Column 4,
Line 47, please add -- Illustrative catalyst precursors of the invention include: --.

Column 5,
Line 24, please replace "$Al(R^2)_5X^1_{3-5}$" with -- $Al(R^2)_sX^1_{3-s}$ --.

Column 16,
Line 44, please replace "results are own" with -- results are shown --.

Column 17,
Line 32, please replace "$[Ph_3C[]B(C_6F_5)_4]$" with -- $[Ph_3C][B(C_6F_5)_4]$ --.

Signed and Sealed this

Twenty-third Day of April, 2002

Attest:

Attesting Officer

JAMES E. ROGAN
*Director of the United States Patent and Trademark Office*